United States Patent [19]

Imai et al.

[11] Patent Number: 5,043,509

[45] Date of Patent: Aug. 27, 1991

[54] SHAPED CATALYST PARTICLES UTILIZABLE FOR THE CONVERSION OF ORGANIC COMPOUNDS

[75] Inventors: Tamotsu Imai, Mt. Prospect; Paul T. Barger, Arlington Heights; Harold U. Hammershaimb, Western Springs, all of Ill.

[73] Assignee: UOP, Des Plaines, Ill.

[21] Appl. No.: 395,939

[22] Filed: Aug. 18, 1989

[51] Int. Cl.$^5$ .............................. C07C 2/68; C07C 2/02
[52] U.S. Cl. ...................... 585/466; 585/468; 585/529; 585/533; 502/527
[58] Field of Search .............. 585/466, 468, 529, 533; 502/527

[56] References Cited

U.S. PATENT DOCUMENTS

| | | | |
|---|---|---|---|
| 2,586,852 | 2/1952 | Morrell | 252/435 |
| 2,644,800 | 7/1953 | Mottern et al. | 252/463 |
| 2,650,201 | 8/1953 | Mavity | 252/435 |
| 2,833,727 | 5/1958 | Mavity et al. | 252/435 |
| 2,871,199 | 1/1959 | Bielawski et al. | 252/435 |
| 3,112,350 | 11/1963 | Bielawski | 260/683.15 |
| 3,966,644 | 6/1976 | Gustafson | 252/455 R |
| 4,028,227 | 6/1977 | Gustafson | 208/216 |
| 4,051,191 | 9/1977 | Ward | 585/466 |
| 4,224,185 | 9/1980 | Wristers | 252/430 |
| 4,328,130 | 5/1982 | Kyan | 252/477 R |
| 4,342,643 | 8/1982 | Kyan | 208/134 |
| 4,370,492 | 1/1983 | Wunder et al. | 560/245 |
| 4,391,740 | 7/1983 | Gibson | 252/470 |
| 4,394,303 | 7/1983 | Gibson | 252/470 |
| 4,441,990 | 4/1984 | Huang | 208/111 |
| 4,489,173 | 12/1984 | Gibson | 502/313 |
| 4,495,307 | 1/1985 | Clements | 502/305 |
| 4,534,855 | 8/1985 | Silverman | 208/253 |
| 4,606,815 | 8/1986 | Gibson | 208/210 |
| 4,652,687 | 3/1987 | Imai et al. | 585/319 |
| 4,717,781 | 1/1988 | Imai et al. | 585/441 |

*Primary Examiner*—Anthony McFarlane
*Assistant Examiner*—Nhat Phan
*Attorney, Agent, or Firm*—Thomas K. McBride; Raymond H. Nelson

[57] ABSTRACT

Catalyst particles which are employed in reactions involving the conversion of organic compounds should possess a desired configuration in order to maintain a desired voidage which will permit passage of the feedstock through the catalyst bed during the conversion reaction. Solid phosphoric acid catalysts which comprise an admixture of an acid of phosphorus and a solid binder such as a siliceous material may be formed into polylobular, tubular, ridged, fluted, or channeled cylindrical particles which will permit a sufficient amount of voidage in the catalyst bed to be maintained even though the catalyst particles will swell during the reaction due to the formation of coke on the surface thereof.

16 Claims, No Drawings

SHAPED CATALYST PARTICLES UTILIZABLE FOR THE CONVERSION OF ORGANIC COMPOUNDS

BACKGROUND OF THE INVENTION

Solid catalyst particles are utilizable for many processes involving the conversion of organic compounds. A particular example of solid catalyst particles comprises solid phosphoric acid which comprises a calcined mixture of an acid of phosphorus and a porous binder material. These solid phosphoric acid catalysts are effective in the polymerization of normally gaseous olefins to form normally liquid hydrocarbons. In addition, solid phosphoric acid catalysts are very useful in catalyzing the alkylation of aromatic hydrocarbons with alkylating agents such as olefins, aliphatic halides, etc. to form useful products.

The catalyst is composed of a support or substrate portion onto which is incorporated an acid fraction for catalytic activity. It is believed that the substrate portion is formed from the silica-phosphoric acid reaction, principally silicon orthophosphate, $Si_3(PO_4)_4$, silicon pyrophosphate, $SiP_2O_7$, as well as derivatives of these compounds. The catalyst is typically prepared by mixing silica with phosphoric acid followed by extrusion and calcination. The reactions are simply illustrated as follows:

$$3SiO_2 + 4H_3PO_4 \rightarrow Si_3(PO_4)_4 + 6H_2O$$

$$SiO_2 + 2H_3PO_4 \rightarrow SiP_2O_7 + 3H_2O$$

The above reactions indicate that the phosphoric acid will react with silica to yield both types of phosphates depending upon stoichiometry and reaction conditions. The silicon orthophosphate can also be dehydrated during drying to give the silicon pyrophosphate, and this is believed to be the alternative mechanism for the silicon pyrophosphate formation. The silicon ortho- to pyrophosphate conversion also depends on factors such as temperature and hydration, as illustrated by the following equations:

$$Si_3(PO_4)_4 + 2H_3PO_4 \rightarrow 3SiP_2O_7 + 3H_2O$$

$$Si_3(PO_4)_4 + heat \rightarrow 2SiP_2O_7 + SiO_2$$

The preparation of these catalysts is known in the art as, for example, U.S. Pat. No. 2,586,852 which describes a solid phosphoric acid comprising a mixture of kaolin, a crystalline silica and phosphoric acid. Other patents which describe various methods of forming this catalyst composite include U.S. Pat. Nos. 2,650,201, 2,833,727, 2,871,199, and 3,112,350.

One disadvantage which may occur during the use of these catalyst composites during a polymerization or alkylation reaction is that the catalyst particles may tend to disintegrate and form solid beds through which the feedstock encounters difficulty in passage through the catalyst bed. Likewise, the catalyst particle, if not disintegrated, may also possess a tendency to increase in volume or swell due to the deposition of coke thereon, thereby further reducing the space between the particles with attendant difficulty of passage through the bed.

It is therefore apparent that the amount of space between the catalyst particles is important and indeed may be considered critical in nature in order to avoid an excessive pressure drop. Inasmuch as the space between the catalyst particles or voidage is critical it is necessary to provide catalyst particles which will not tend to reduce this voidage but will provide a sufficient amount of voidage to enable any expansion of the catalyst particle without excessive loss of voidage and thereby allow a concurrent stability of pressure to be maintained.

The prior art is replete with patents showing various shaped catalyst particles. However, as will hereinafter be shown in great detail, these particles comprise bases having a catalytically active metal deposited thereon or zeolitic catalysts which may not contain a catalytic metal. Examples of these prior patents include U.S. Pat. No. 3,966,644 which shows a porous hydrotreating catalyst particle comprising a major portion of alumina and a minor portion of silica having a catalytic metal such as molybdenum, cobalt nickel, or mixtures thereof deposited on this catalyst base. U.S. Pat. Nos. 4,328,130 and 4,342,643 show shaped channeled catalysts which comprise a refractory oxide such as alumina, silica, silica-alumina, magnesium, etc. containing active transition metals in the form of metals, metal oxides, metal sulfides, and, if so desired, an aluminosilicate zeolite. U.S. Pat. No. 4,370,492 discloses a carrier such as a silicic acid having a noble metal composited thereof. Likewise, U.S. Pat. No. 4,495,307 also shows a shaped catalyst comprising a catalyst base such as alumina, silica or silica-alumina, having a hydrogenation metal selected from Group VIB and Group VIII of the Periodic Table composited thereon. U.S. Pat. No. 4,391,740 is drawn to a catalyst for hydroprocessing heavy carbonaceous feedstocks in which an elongated extrudate of a catalyst of a base such as alumina or silica having a catalytic metal such as molybdenum, tungsten, nickel or cobalt composited thereon, the preferred shape for this catalyst being oval or elliptical in configuration with or without bumps. U.S. Pat. Nos. 4,394,303, 4,489,173 and 4,606,815 all disclose shaped catalysts for hydroprocessing hydrocarbon feedstocks of lobular configuration, said bases comprising refractory inorganic oxides or clays having a catalytic metal such as molybdenum, tungsten, nickel or cobalt composited thereon. Likewise other shaped catalyst particles having lobular shapes are set forth in U.S. Pat. Nos. 4,028,227, 4,495,307 and 4,534,855. The first of these references utilizes a catalyst base such as alumina impregnated with cobalt and/or molybdenum while the latter two comprise only alumina.

Other prior U.S. patents disclose shaped particles such as U.S. Pat. No. 4,441,990. This patent discloses hollow shaped catalytic extrudates which are essentially rectangular or triangular in cross section. The catalyst particles comprise support materials onto which metals may be added. Particular catalyst particles which are enumerated include alumina or alumina as a support in admixture with a zeolite, and which may contain cobalt, molybdenum oxides, copper or zinc oxides as an added metal. Another prior U.S. Patent is U.S. Pat. No. 2,644,800 which discloses a shaped catalyst having a packed catalytic reactor comprising a plurality of flanges around a central post element, the support comprising a cylindrical metal having a catalyst surface. In addition, U.S. Pat. No. 4,224,185 discloses a formed, shaped solid catalyst in which a solid catalyst particle is admixed with a fibrillatable polyolefin followed by mechanically shearing the mixture to form a mat of catalyst particles which are entrapped in the polyolefin and thereafter mechanically shaping the mat to provide the desired catalyst particles. Likewise, U.S. patents which disclose shaped catalyst particles include U.S. Pat. Nos. 4,652,687 and 4,717,781. These patents show shaped particles which may be polylobular or cylindrical in configuration. However, these particles are utilized as oxidation catalysts and comprise a Group VIII noble metal, a Group IVA metal and a Group IA or IIA metal composited on a metal oxide support such as alumina.

However, to reiterate, it is to be noted that none of the above shaped catalysts comprise a shaped particle which consists of an admixture of an acid of phosphorus with a porous binder, said admixture being formed with a desired configuration, as is the case of the present invention.

BRIEF SUMMARY OF THE INVENTION

This invention relates to shaped solid particles which are utilizable for the conversion of organic compounds and particularly to the polymerization or alkylation of organic hydrocarbons. In addition, the invention also relates to a process employing these shaped catalyst particles to obtain desirable products as a result of the processes in which the catalysts are employed. By utilizing a catalyst which possesses a shaped form such as a polylobular configuration it is possible to effect a process in such a manner whereby the possibility of a disadvantageous pressure drop occurring is greatly diminished.

It is therefore an object of this invention to provide a shaped catalyst particle utilizable in a hydrocarbon conversion process such as polymerization or alkylation which will possess the ability to maintain a desired degree of voidage between the particles, thus permitting the uninterrupted flow of feedstock to be converted through a catalyst bed.

A further object of this invention is to provide an organic compound conversion process utilizing the shaped catalyst particles of the present invention to obtain the desired product in an economical manner.

In one aspect an embodiment of this invention resides in a solid catalyst composite for the conversion of organic compounds, which consists of a shaped extrudate having a ratio of exterior surface area to catalyst volume greater than $$\left[\frac{2}{L} + \frac{4}{D}\right]$$

in which D is the largest representative diameter and L is the length of said extrudate, comprising a solid binder admixed with a phosphoric acid.

Another embodiment of this invention resides in a process for the conversion of an organic compound which comprises contacting said organic compound at conversion conditions with a solid catalyst, which consists of a shaped extrudate having a ratio of exterior surface area to catalyst volume greater than $$\left[\frac{2}{L} + \frac{4}{D}\right]$$

in which D is the largest representative diameter and L is the length of said extrudate, comprising a solid binder admixed with a phosphoric acid, and recovering the resultant conversion product.

A specific embodiment of this invention resides in a solid catalyst composite for the conversion of organic compounds consisting of a polylobular shaped particle containing from 3 to about 8 lobes comprising diatomaceous earth admixed with polyphosphoric acid in which said phosphoric acid is present in an amount greater than about 10% by weight of the composite.

A specific embodiment of this invention is found in a process for the conversion of organic compounds which comprises contacting an olefinic feedstream containing from 2 to about 6 carbon atoms at a temperature in the range of from about 100° to about 400° C. and a pressure in the range of from about 1 to about 500 atmospheres with a solid catalyst comprising a polylobular shaped particle comprising diatomaceous earth admixed with phosphoric acid and recovering the resultant polymerized product.

Other objects and embodiments will be found in the following further detailed description of the invention.

DETAILED DESCRIPTION OF THE INVENTION

As hereinbefore set forth the present invention is concerned with a shaped catalyst particle which is utilizable in catalytic conversion processes whereby various organic compounds are converted to useful products. As was hereinbefore described, catalyst particles when formed into a catalyst bed in a reactor may tend to disintegrate or break down during the process in which they are employed. Alternatively, if the catalyst does not disintegrate or break down it may have a tendency to swell. Either the disintegration or swelling of the catalyst in the catalyst bed will tend to minimize the space between the particles and thus contribute to a pressure drop between the entrance to the bed and the exit from the bed. By clogging the spaces between the catalyst particles it will therefore require a continued increase in pressure or necessitate the removal of the catalyst bed and replacement thereof in order to provide a workable process. In order to minimize the necessity for replacement of catalyst or use of increased pressure, both of which will contribute to an increase in the cost of the process and thus perhaps render the process uneconomical to operate it has now been discovered that these difficulties may be overcome by employing catalyst particles which possess a definite configuration. By utilizing a cylindrical or polylobular shaped particle of the type hereinafter set forth in greater detail it is possible to maintain the voidage between the catalyst particles and thus prevent a loss of pressure with an excessive pressure drop through the bed of the catalyst. We have now discovered that solid phosphoric acid catalyst particles may be configured in a shaped form such as a polylobular, tubular, ridged, fluted or channeled cylindrical shape and thus used in either polymerization or alkylation reactions, said particles even though they may swell or increase in volume in an amount in the range of from about 10% to about 150% by volume of the original size, and still provide sufficient voidage so that there is little, if any, pressure drop through the catalyst bed.

The solid phosphoric acid catalyst of the present invention will comprise a solid binder admixed with an acid of phosphorus and then one of the essential and active ingredients of the solid catalysts of this invention for use in organic reactions is an acid of phosphorus, preferably one in which the phosphorus has a valence of 5. The acid may constitute from about 10% to about 80% of the catalyst mixture ultimately produced. Of the various acids of phosphorus, orthophosphoric acid ($H_3PO_4$) and pyrophosphoric acid ($H_4P_2O_7$) find general application in the primary mixtures, due mainly to the cheapness and to the readiness with which they may be procured, although the invention is not restricted to their use, but may employ any of the other acids of phosphorus insofar as they are adaptable. However, it is not intended to infer that the different acids of phosphorus which may be employed will produce catalysts which have identical effects upon any given organic reactions as each of the catalysts produced from different acids and by slightly varying procedures will exert its own characteristic action.

In using orthophosphoric acid as one of the primary ingredients, different concentrations of the aqueous solutions may be employed, for example, acid containing from approximately 75 to 100% $H_3PO_4$ or orthophosphoric acid containing some free phosphorus pentoxide may be used. By this is meant that the ortho acid may contain a definite percentage of the pyro acid corresponding to the primary phase of dehydration of orthophosphoric acid. Within these concentration ranges the acids will be liquids of varying viscosities and readily mixed with solid siliceous adsorbents.

Triphosphoric acid which may be represented by the formula: $H_5P_3O_{10}$ may also be used as one of the starting materials for the preparation of the catalyst of this invention. These catalytic compositions may also be prepared from the polycyclic aromatic hydrocarbons, the siliceous adsorbents, and a phosphoric acid mixture containing orthophosphoric acid, pyrophosphoric acid, triphosphoric acid and other polyphosphoric acids.

A phosphoric acid mixture which is generally referred to as polyphosphoric acid may also be employed in this process. Polyphosphoric acid is formed by heating orthophosphoric acid or pyrophosphoric acid or mixtures thereof in suitable equipment such as carbon lined trays heated by flue gases or other suitable means to produce a phosphoric acid mixture generally analyzing from about 79% to about 85% by weight of $P_2O_5$. Such a liquid mixture of phosphoric acids with 79.4% $P_2O_5$ content was found by analysis to contain 24.5% of orthophosphoric acid ($H_3PO_4$), 45.2% of pyrophosphoric acid ($H_4P_2O_7$), 26.0% of triphosphoric acid ($H_5P_3O_{10}$), and 4.3% by weight of unidentified phosphoric acids. Another polyphosphoric acid mixture somewhat more concentrated than the one just referred to and having a $P_2O_5$ content of 84% by weight was found by analysis to contain about 57% by weight of triphosphoric acid ($H_5P_3O_{10}$), 17% by weight of hexametaphosphoric acid ($HPO_3)_6$, 11% by weight of pyrophosphoric acid ($H_4P_2O_7$), 5% by weight of orthophosphoric acid ($H_3PO_4$) and 10% by weight of unidentified phosphoric acids.

Another acid of phosphorus which may be employed in the manufacture of a composite catalyst according to the present invention is tetraphosphoric acid. It has the general formula: $H_6P_4O_{13}$ which corresponds to the double oxide formula: $3H_2O.2P_2O_5$ which in turn may be considered as the acid resulting when three molecules of water are lost by four molecules of orthophosphoric acid $H_3PO_4$. The tetraphosphoric acid may be manufactured by gradual or controlled dehydration or heating of orthophosphoric acid and pyrophosphoric acid or by adding phosphoric pentoxide to these acids in proper amounts. When the latter procedure is followed, phosphoric anhydride is added gradually until it amounts to 520% by weight of total water present. After a considerable period of standing at ordinary temperature, the crystals of the tetraphosphoric acid separate from the viscous liquid and it is found that these crystals melt at approximately 93° F. and have a specific gravity of 1.1886 at a temperature of 60° F. However, it is unnecessary to crystallize the tetraphosphoric acid before employing it in the preparation of the solid catalyst inasmuch as the crude tetraphosphoric acid mixture may be incorporated with the polycyclic aromatic hydrocarbon and the solid siliceous adsorbent.

The materials which may be employed as adsorbents or carriers for oxygen acids of phosphorus are divided roughly into two classes. The first class comprises materials of predominantly siliceous character and includes diatomaceous earth, kieselguhr, and artificially prepared porous silica. The second class of materials which may be employed either along with or in conjunction with the first class comprises generally certain members of the class of aluminum silicates and includes such naturally occurring substances as various fuller's earths and clays such as bentonite, montmorillonite, acid treated clays and the like. Each adsorbent or supporting material which may be used will exert its own specific influence upon the net effectiveness of the catalyst composite which will not necessarily be identical with that of other members of the class.

The catalyst composites which are utilized in the present invention are prepared by admixing an oxygen acid of phosphorus and a solid binder which, in the preferred embodiment of the invention, comprises a siliceous material, at a temperature in the range of from about 10° to about 230° C., and preferably at to form a composite, the oxygen a temperature of from about 95° to about 200° C. to form a composite, the oxygen acid of phosphorus being present in said composite in an amount greater than about 10% by weight. As an example of this, a composite may be formed by heating polyphosphorus acid (82% $P_2O_5$ content) to a temperature of about 170° C. and thereafter mixing this hot acid with diatomaceous earth which has previously been at room temperature. The polyphosphorus acid and diatomaceous earth form a composite which has the weight ratio of phosphorus pentoxide to diatomaceous earth in a range of from about 2.5 to about 7.5. This composite is slightly moist to almost dry in appearance but becomes plastic when subjected to pressure in a hydraulic press type or auger type extrudate by which the composite is formed into the desired shaped particles.

As was previously discussed the catalyst particles may be polylobular in configuration and may contain from 3 to about 8 lobes, thus enabling the catalyst, when loaded into a bed, to maintain a sufficient voidage in the bed whereby an uninterrupted flow of feedstock will pass through the bed without a depreciable loss of pressure even though the catalyst particle will swell and increase in volume. The catalytic particles may range in length from about 0.075 to about 0.75 inches and will have a ratio of exterior surface to catalyst volume greater than $[4/D+2/L]$, where D is the largest representative diameter and L the length of the extrudate. In addition, the die through which the dough is extruded will be configured to form lobes, the length of each lobe ranging from about 0.01 D to about 0.3 D while the average width of the lobe will range from about 0.01 D to 0.5 D. By forming a catalyst which possesses these particular configurations, it is possible to obtain a catalyst which possesses a greater effectiveness factor with a corresponding stability than was obtained when utilizing catalysts of more conventional shapes. The finished particles may be either solid or, if so desired, possesses an aperture through the central part of the particle. The resultant catalyst composite which is extruded through the die is still in a heated condition and the die through which the catalyst is extruded will also be preheated to a predetermined temperature as, for example, about 170° C. The extruded catalyst particles in polylobular shape are then calcined by heating in air, nitrogen, flue gas, or some other inert gas at a temperature of from about 300° to about 400° C. and preferably at a temperature of from about 550° to about 675° C. for a period of time which may range from about 0.25 to about 8 hours, and preferably from about 0.5 to about 2 hours.

Another catalyst composite of the present invention comprising an admixture of a solid binder and an acid of phosphorus may be simply tubular in configuration or may comprise a tube having the interior section of the tube filled with a plurality of intersecting veins that give the particle a cartwheel shape. The catalytic particles may range in length from about 0.050 to about 0.75 inches and will have a ratio of shape surface to gross catalyst volume greater than $[4/D + 2/L]$, where D is the average outside diameter of the entire particle and L is the length of the extrudate. The term shape surface refers to the macroscopic surface area of the catalyst for all surfaces of the catalyst, including the interior walls of the channels and excludes the surface area associated with any microscopic pores. The term gross volume means the solid catalyst volume which includes the volume of the channels. The relative inside and outside diameters of the channels are limited to provide to a ratio of $d_o/d_i$ which is between 1.1 and 8.0 where $d_i$ is the largest transverse dimension across the inside of any channel and $d_o$ is the dimension to the outside of walls surrounding the channel, taken along the line of dimension $d_i$. This ratio of channel diameters is chosen to provide channels large enough for flow purposes and adequate wall thickness around the channels for structural integrity of the support.

Still another form or shape of the catalyst comprising an admixture of a solid binder and an acid of phosphorous will comprise a cylinder having ridges, flutes or channels, the number of ridges, flutes or channels on the surface of the cylinder ranging from 2 to about 10. As in the case of the polylobular catalyst particles they may be solid or possess an aperture and will have a ratio of exterior surface to catalyst volume greater than $$\left[\frac{4}{D} + \frac{2}{L}\right]$$

The resulting catalyst which has been calcined is active for promoting the polymerization of olefinic hydrocarbons, particularly for polymerizing normally gaseous olefinic hydrocarbons to form normally liquid hydrocarbons suitable for use as constituents of gasoline. When employed in the conversion of olefinic hydrocarbons into polymers, the calcined catalyst formed as hereinbefore set forth is preferably employed as a bed in a heated reactor which is generally made from steel, and through which the preheated hydrocarbon fraction is directed. Thus, the solid catalyst of this process may be employed for treating mixtures of olefin-containing hydrocarbon vapors to effect olefin polymerization, but the same catalyst may also be used at operating conditions suitable for maintaining liquid phase operation during polymerization of olefinic hydrocarbons such as butylenes, to produce gasoline fractions. When employed in the polymerization of normally gaseous olefins, the formed and calcined catalyst particles are generally placed in a vertical, cylindrical treating tower and the olefin-containing gas mixture is passed downwardly therethrough at a temperature of from about 150° to about 400° C. and at a pressure of from about 1 to about 100 atmospheres. These conditions are particularly applicable when dealing with olefin-containing material such as stabilizer reflux which may contain from approximately 10 to 50% or more of propylene and butylenes. When operating on a mixture comprising essentially butanes and butylenes, this catalyst is effective at conditions favoring the maximum utilization of both normal butylenes and isobutylene which involves mixed polymerization at temperatures from about 100° to about 400° C. and a pressure from about 5 to about 500 atmospheres.

The catalyst of this invention is also useful in the alkylation of aromatic hydrocarbons with an alkylating agent. The alkylating agent which may be charged to the alkylation reaction zone may be selected from a group of diverse materials including monoolefins, diolefins, polyolefins, acetylenic hydrocarbons, and also alkylhalides, alcohols, ethers, esters, the latter including the alkylsulfates, alkylphosphates, and various esters of carboxylic acids. The preferred olefin-acting compounds are olefinic hydrocarbons which comprise monoolefins containing one double bond per molecule. Monoolefins which may be utilized as olefin-acting compounds in the process of the present invention are either normally gaseous or normally liquid and include ethylene, propylene, 1-butene, 2-butene, isobutylene, and the higher molecular weight normally liquid olefins such as the various pentenes, hexenes, heptenes, octenes, and mixtures thereof, and still higher molecular weight liquid olefins, the latter including various olefin polymers having from about 9 to about 18 carbon atoms per molecule including propylene trimer, propylene tetramer, propylene pentamer, etc. Cycloolefins such as cyclopentene, methylcyclopentene, cyclohexene, methylcyclohexene, etc., may also be utilized, although not necessarily with equivalent results. Other hydrocarbons such as paraffins, naphthenes, and the like containing 2 to 18 carbon atoms may also be present in the alkylating agent. When the catalyst of the present invention is used for catalyzing an aromatic alkylation reaction, it is preferred that the monoolefin contains at least 2 and not more than 14 carbon atoms. More specifically, it is preferred that the monoolefin is propylene.

The aromatic substrate which is charged to the alkylation reaction zone in admixture with the alkylating agent may be selected from the group of aromatic compounds which include individually and in admixture benzene, monocyclic alkyl substituted benzenes such as toluene, o-xylene, m-xylene, p-xylene, mesitylene (1,3,5-trimethylbenzene), pseudocumene (1,2,4-trimethylbenzene), hemimellitene (1,2,3-trimethylbenzene), ethylbenzene, o-diethylbenzene, m-diethylbenzene, p-diethylbenzene, etc., and polycyclic aromatic compounds such as naphthalene, alkyl substituted naphthalenes, anthrcenes, etc.

In a continuous process for alkylating aromatic hydrocarbons with olefins, the previously described reactants are continuously fed into a pressure vessel containing solid phosphoric acid catalyst of this invention. The feed admixture may be introduced into the alkylation reaction zone containing the alkylation catalyst at a constant rate, or alternatively, at a variable rate. Normally, the aromatic substrate and olefinic alkylating agent are contacted at a molar ratio of from about 1:1 to 20:1 and preferably from about 2:1 to 10:1. The preferred molar feed ratios help to maximize the catalyst life cycle by minimizing the deactivation of the catalyst by coke and heavy material deposition upon the catalyst. The catalyst may be contained in one bed within a reactor vessel or divided up among a plurality of beds within a reactor. The alkylation reaction system may contain one or more reaction vessels in series. The feed to the reaction zone can flow vertically upwards, or downwards through the catalyst bed in a typical plug flow reactor, or horizontally across the catalyst bed in a radial flow type reactor.

In some cases, in order to maintain the reaction temperature in the preferred range and thus reduce the formation of unwanted polyalkylaromatics, it may be desirable to quench the reactants to dissipate heat of reaction. A quench stream comprised of the alkylating agent olefin, the alkylating agent or a portion of the reactor effluent stream, or mixtures thereof may be injected into the alkylation reactor system in order to dissipate heat and supply additional amounts of olefin alkylating agent and unreacted aromatic substrate at various locations within the reaction zone. This is accomplished for example in a singlestage reactor by multiple injection of the aforementioned quench stream components into the reaction zone via strategically placed inlet lines leading into said reaction zone. The amount and composition of quench material injected into either a single stage reaction system or multi-stage reaction system may be varied according to need. Benefits resulting from multiple quench injection include elimination of costly cooling apparatus in the process, improved selectivity to formation of the desired alkylaromatic compound, provision for a larger heat sink and optimization of the olefin to aromatic compound molar ratio throughout the reaction zone, thus resulting in increased yield of the desired monoalkylated aromatic compound.

Temperatures which are suitable for use in the process herein are those temperatures which initiate a reaction between an aromatic substrate and the particular olefin used to selectively produce the desired monoalkylaromatic compound. Generally, temperatures suitable for use are from about 100° to about 390° C., especially from about 150° to about 275° C. Pressures which are suitable for use herein preferably are above about 1 atmosphere but should not be in excess of about 130 atmospheres. An especially desirable pressure range is from about 10 to about 40 atmospheres; with a liquid hourly space velocity (LHSV) based upon the benzene feed rate of from about 0.5 to about 50 hr$^{-1}$. It should be noted that the temperature and pressure combination used herein is to be such that the alkylation reaction takes place in essentially the liquid phase. In a liquid phase process for producing alkylaromatics, the catalyst is continuously washed with reactants, thus preventing buildup of coke precursors on the catalyst. This results in reduced amounts of carbon forming on said catalyst in which case, catalyst cycle life is extended as compared to a gas phase alkylation process in which coke formation and catalyst deactivation is a major problem.

Additionally, a regulated amount of water is preferably added to the alkylation reaction zone. In order to substantially prevent loss of water from the catalyst and subsequent decrease in catalyst activities, an amount of water or water vapor such as steam is added to the charge so as to substantially balance the water vapor pressure of the alkylation catalyst hereinabove described. This amount of water varies from about 0.01 to 6% by volume of the organic material charged to the alkylation reaction zone. The water is then typically removed with the light by-product stream recovered in the first separation zone.

As was hereinbefore set forth, when employing a continuous type of operation in which the solid phosphoric acid catalysts are disposed as a fixed bed in a reaction zone by utilizing the tubular or polylobular shaped particle of the present invention, it is possible to maintain a proper operating condition involving pressure. This proper operating pressure will remain fairly constant even though the catalyst particle will swell during the use thereof due to various conditions including the deposition of coke on the surface of the catalyst particle. Even though the particle size or volume may be increased from about 10% to about 150% of the original size or volume of the particle it will still be possible to retain a sufficient amount of voidage in the reactor and thus enable the process to be maintained over fairly constant operating conditions.

While the above discussion has centered mainly on the use of a continuous type of operation it is also contemplated that the conversion of organic compounds may be effected in a batch type operation. When this type of operation is employed a quantity of the desired catalyst is placed in a suitable apparatus, one example of which comprises an autoclave of the rotating or stirred type, the organic compound or compounds to be converted may then be charged to the apparatus while the apparatus is heated to the desired operating temperature of from about 100° to about 400° C. and at pressures ranging from about atmospheric to about 100 atmospheres or more. The pressure does not appear to be a critical variable inasmuch as the process may be carried out in either a liquid or vapor phase, thus the pressure which is utilized to effect the reaction may be selected purely from the most advantageous pressure based upon economic consideration and obtain the stability of the particular reactants which are charged to the process under the necessary processing conditions. At the end of a predetermined residence time the apparatus and contents thereof are allowed to cool to room temperature, any excess pressure is vented and the desired reaction product comprising, for example, the polymerized olefinic hydrocarbon or the alkylaromatic compound is recovered, separated from the catalyst by conventional means such as filtration, centrifugation, etc., further separated from any other unreacted starting materials by conventional means such as fractional distillation, crystallization, etc. and recovered.

The following examples are given as illustrative embodiments of the present invention with relation to the shaped catalyst particles. However, it is to be understood that this invention is not necessarily limited thereto.

EXAMPLE 1

Cylindrical extrudates of solid catalyst composite comprised of polyphosphoric acid and a kieselguhr binder and containing 73.1 weight percent phosphoric acid as polyphosphoric acid were loaded into a reactor and contacted with a feed stream consisting of $C_3$ and $C_4$ paraffins and olefins with about 250 ppm $H_2O$ to maintain catalyst hydration for sufficient time to produce 40 gallons of olefin polymer product per pound of catalyst. During the run the pressure drop across the reactor increased from about 2 pounds per square inch gauge (psig) to about 36 psig. At the completion of this run the spent catalyst was removed from the reactor tube and inspected. Representative samples from 5 foot and 10 foot depths in the reactor tube showed substantial swelling compared with a retained sample of the fresh catalyst such that the catalyst particles were compressed into a single mass with with greatly reduced voidage.

EXAMPLE 2

A laboratory plant test has been employed to quantitate the amount of swelling that occurs with catalyst particles of the formulation of the current invention during use for olefin polymerization. For each test 20 pellets of an extrudated solid catalyst composite comprised of polyphosphoric acid and a kieselguhr binder were shaped into 0.3×0.4 cm cubes. Each cube was measured, weighed and loaded into a ⅞ inch ID reactor using five stainless steel baskets to isolate each catalyst cube from all others. Three tests were conducted in which a hydrocarbon feed comprised of equal amounts by weight of propylene and a commercially-produced propylene polymer product with 1 weight percent added $H_2O$ was feed to the reactor at 375° C., 300 psig, and $17_{hr}^{-1}$ WHSV for 4, 20 and 30 hours. At the end of the specified time the spent catalyst cubes were recovered and weighed and measured. The weight and volume gains as percent of fresh catalyst weight and volume are tabulated in Table 1.

TABLE 1

| Test Number | Hours on Stream | % Weight Gain | % Volume Gain |
|---|---|---|---|
| 1 | 4 | 9 ± 7 | 26 ± 11 |
| 2 | 20 | 34 ± 12 | 91 ± 25 |
| 3 | 30 | 55 ± 15 | 122 ± 32 |

EXAMPLE 3

According to engineering calculations and engineering design information which has been developed over the years, the physical properties of solid phosphoric acid catalysts comprising an admixture of acid of phosphorus and a solid binder will possess the following properties.

TABLE 2

Catalyst Physical Properties

| Shape | ABD gm/cc | Piece Density gm/cc | Diameter $D_1$ mm | Diameter $d_1$ mm | Lob Length $l_1$ mm | Lob Width $W_1$ mm | Particle Length mm |
|---|---|---|---|---|---|---|---|
| Solid Cylinder | 0.990 | 1.65 | 4.5 | — | — | — | 6 |
| Quadralobe | 0.908 | 1.65 | — | 2.8 | 0.85 | 2 | 6 |
| Tubular Cyl. | 0.795 | 1.65 | 4.5 | 2.0 | — | — | 6 |

In addition, when utilized as a catalyst in a reactor the catalyst particles will possess a voidage according to the following table.

TABLE 3

| Shape | ABD | Piece Density | Voidage |
|---|---|---|---|
| Solid Cylinder | 0.990 | 1.65 | 0.400 |
| Quadralobe | 0.908 | 1.65 | 0.450 |
| Tubular Cylinder | 0.795 | 1.65 | 0.518 |

According to engineering calculations the performance of solid phosphoric acid catalysts having various shapes will perform according to Table 3 if utilized as a polymerization catalyst in a reactor in which a feed comprising a mixture of about 50/50% of propylene and propane or a feed of approximately 50/50% butylene and butane or a feed in approximately the same ration of a mixture of propylene and butylene with propane and butane is passed over the catalyst in a tubular reactor which is maintained at an inlet temperature of about 200° C. and a pressure of 1,000 psig at a liquid hourly space velocity of 2.5.

TABLE 4

Calculated Performance

| Relative Time on Stream | Catalyst Weight Gain % | Catalyst Volume Gain % | SOLID CYLINDER | | | QUADRALOBE | | | TUBULAR CYLINDER | | |
|---|---|---|---|---|---|---|---|---|---|---|---|
| | | | Solid Fraction | Void Fraction | ΔP psi | Solid Fraction | Void Fraction | ΔP psi | Solid Fraction | Void Fraction | ΔP psi |
| 0 | 0 | 0 | 0.600 | 0.400 | 2.9 | 0.550 | 0.450 | 2.2 | 0.482 | 0.518 | 1.4 |
| 25 | 6.5 | 11.8 | 0.672 | 0.328 | 5.2 | 0.616 | 0.384 | 3.5 | 0.540 | 0.460 | 2.0 |
| 50 | 12.1 | 21.8 | 0.732 | 0.268 | 9.5 | 0.671 | 0.329 | 5.6 | 0.588 | 0.412 | 2.8 |
| 75 | 17.4 | 31.8 | 0.792 | 0.208 | 20.3 | 0.726 | 0.274 | 9.7 | 0.636 | 0.364 | 4.0 |
| 100 | 22.5 | 40.9 | 0.846 | 0.154 | 50 | 0.776 | 0.224 | 17.8 | 0.680 | 0.320 | 5.9 |
| 125 | 27.5 | 50.0 | 0.900 | 0.100 | 183 | 0.825 | 0.175 | 37 | 0.723 | 0.277 | 9.1 |
| 150 | 32.4 | 59.1 | 0.954 | 0.046 | >1000 | 0.875 | 0.125 | 102 | 0.766 | 0.234 | 15.1 |

It is to be noted from the above calculations that catalyst particles which possess a quadralobe or tubular cylindrical shape will maintain a sufficient amount of voidage to permit passage of the feed over the catalyst without resulting in a pressure drop sufficient to render the process inoperable. For example, at a relative time of 100 the pressure drop when utilizing a solid cylinder shaped particle will result in a pressure drop of 50 psi as compared to a pressure drop of 17.8 psi for the quadralobular shaped particle and a pressure drop of only 5.9 psi for a tubular cylindrical shaped particle. The pressure drop or P at a relative time of 150 shows that the solid cylinder is over 1,000 psi as compared to 102 psi for the quadralobe and 15.1 psi for the tubular cylinder. This pressure drop would effectively halt the flow of the feed through the reactor in the case when utilizing a solid cylinder. Similar calculations should also show the same results could be obtained when using catalyst particles which possess configurations such as ridged, fluted or channeled cylindrical shapes.

It is therefore readily apparent from the above calculations that the use of catalyst particles which possess a desired configuration will permit a sufficient amount of voidage to be maintained during the operation when compared to catalyst particles which have heretofore been employed in this type of reaction.

We claim as our invention:

1. A process for the conversion of an organic compound which comprises contacting said organic compound at conversion conditions with a solid catalyst to yield a conversion product, said catalyst consisting of a shaped extrudate having a ratio of exterior surface area to catalyst volume greater than $$\left[\frac{2}{L} + \frac{4}{D}\right]$$

in which D is the largest representative diameter of said extrudate and L is the length of said extrudate, said catalyst comprising a solid binder admixed with a phosphoric acid, and recovering the resultant conversion product.

2. The process of claim 1 in which said conversion conditions include a temperature in the range of from about 100° to about 400° C. and a pressure in the range of from about 1 to about 500 atmospheres.

3. The process of claim 1 in which said conversion process comprises the alkylation of an aromatic compound with an alkylating agent.

4. The process of claim 1 in which said conversion process comprises the polymerization of an olefinic hydrocarbon containing from 2 to about 4 carbon atoms.

5. The process of claim 1 in which said shaped extrudate comprises a polylobular particle containing from 3 to about 8 lobes.

6. The process of claim 1 in which said particle comprises an inorganic oxide.

7. The process as set forth in claim 6 in which said inorganic oxide comprises silicious material selected from the group consisting of diatomaceous earth, kieselguhr, and artificially prepared silica.

8. The process of claim 1 in which said phosphoric acid comprises pyrophosphoric acid.

9. The process of claim 1 in which said phosphoric acid comprises orthophosphoric acid.

10. The process of claim 1 in which said phosphoric acid comprises polyphosphoric acid.

11. The process of claim 1 in which said phosphoric acid comprises tetraphosphoric acid.

12. The process of claim 1 in which said phosphoric acid comprises triphosphoric acid.

13. The process of claim 1 in which said phosphoric acid contains free phosphorous pentoxide.

14. The process of claim 1 wherein said shaped extrudate consists of polylobular, tubular, ridged, fluted or channeled cylindrical shaped particles.

15. The process of claim 14 wherein said shaped extrudate consists of a tubular cylinder.

16. The process of claim 14 wherein said polylobular shaped particle possesses an aperture through a central portion thereof.

* * * * *